(12) United States Patent
Henry

(10) Patent No.: US 11,357,793 B2
(45) Date of Patent: *Jun. 14, 2022

(54) PHARMACEUTICAL FORMULATIONS FOR THE TREATMENT AND PREVENTION OF TRAUMA-INDUCED NEUROPATHOLOGY AND NEURODEGENERATION

(71) Applicant: Sapna Life Sciences Corporation, Burlington (CA)

(72) Inventor: James Lorne Henry, Burlington (CA)

(73) Assignee: Sapna Life Sciences Corporation, Burlington (CA)

( * ) Notice: Subject to any disclaimer, the term of this patent is extended or adjusted under 35 U.S.C. 154(b) by 572 days.

This patent is subject to a terminal disclaimer.

(21) Appl. No.: 16/233,287

(22) Filed: Dec. 27, 2018

(65) Prior Publication Data

US 2019/0125789 A1    May 2, 2019

Related U.S. Application Data

(63) Continuation of application No. 14/921,058, filed on Oct. 23, 2015, now Pat. No. 10,201,569, which is a continuation of application No. 14/148,709, filed on Jan. 6, 2014, now abandoned.

(60) Provisional application No. 61/750,745, filed on Jan. 9, 2013.

(51) Int. Cl.

| | |
|---|---|
| A61K 33/14 | (2006.01) |
| A61K 31/19 | (2006.01) |
| A61K 31/194 | (2006.01) |
| A61K 31/195 | (2006.01) |
| A61K 31/197 | (2006.01) |
| A61K 31/495 | (2006.01) |
| A61K 31/496 | (2006.01) |
| A61K 31/5377 | (2006.01) |
| A61K 31/57 | (2006.01) |
| A61K 33/00 | (2006.01) |
| A61K 45/06 | (2006.01) |
| A61K 31/20 | (2006.01) |
| A61K 31/573 | (2006.01) |
| A61K 31/205 | (2006.01) |

(52) U.S. Cl.
CPC .............. *A61K 33/14* (2013.01); *A61K 31/19* (2013.01); *A61K 31/194* (2013.01); *A61K 31/195* (2013.01); *A61K 31/197* (2013.01); *A61K 31/20* (2013.01); *A61K 31/205* (2013.01); *A61K 31/495* (2013.01); *A61K 31/496* (2013.01); *A61K 31/5377* (2013.01); *A61K 31/57* (2013.01); *A61K 31/573* (2013.01); *A61K 33/00* (2013.01); *A61K 45/06* (2013.01)

(58) Field of Classification Search
None
See application file for complete search history.

(56) References Cited

U.S. PATENT DOCUMENTS

| | | |
|---|---|---|
| 6,245,757 B1 | 6/2001 | Chopp et al. |
| 6,413,999 B1 | 7/2002 | Juurlink et al. |
| 7,399,740 B2 | 7/2008 | Eisenbach-Schwartz et al. |
| 7,473,687 B2 | 1/2009 | Hoffman et al. |
| 7,560,102 B2 | 7/2009 | Eisenbach-Schwartz et al. |
| 7,745,387 B2 | 6/2010 | Bahlmann et al. |
| 7,776,326 B2 | 8/2010 | Milbrandt et al. |
| 7,803,793 B2 | 9/2010 | Zhang et al. |
| 7,846,897 B2 | 12/2010 | Tymianski |
| 7,872,048 B2 | 1/2011 | Simard |

(Continued)

FOREIGN PATENT DOCUMENTS

| | | |
|---|---|---|
| CA | 2625210 A1 | 5/2007 |
| CA | 2831054 C | 8/2016 |

(Continued)

OTHER PUBLICATIONS

Yu, Fengshan et al. "Lithium ameliorates neurodegeneration, suppresses neuroinflammation, and improves behavioral performance in a mouse model of traumatic brain injury." Journal of neurotrauma vol. 29,2 (Year: 2012).*
MediCalc <http://www.scymed.com/en/smnxtb/tbcbgwh1.htm>; accessed Jun. 18, 2021 (Year: 2021).*
International Search Report and Written Opinion of WO2014/108809 dated Jul. 24, 2014.
International Search Report and Written Opinion of WO2014/108807 dated Aug. 22, 2014.
Schumacher, Michael et al. "Progresterone and Progestins: Neuroprotection and Myelin Repair", Current Opinion of Pharmacology, 2008, pp. 740-746.

(Continued)

*Primary Examiner* — Nicole P Babson
(74) *Attorney, Agent, or Firm* — Bereskin & Parr LLP/S.E.N.R.L., s.r.l.; Patricia Folkins

(57) ABSTRACT

Novel multi-component formulations, procedures and methods for use in treating neuropathology and neurodegeneration incident to trauma are provided. Multi-component formulations of the invention comprise biologically active forms of any two, any three, or all four of at least one neurosteroid or neuroactive steroid, such as progesterone or synthetic progestin, at least one anti-epileptic or anticonvulsant, such as gabapentin, pregabalin or valproic acid, at least one NK-1 receptor antagonist, such as aprepitant, casopitant or vestipitant, at least one lithium-containing or lithium-related drug. The provided formulations are configured or adapted to prevent or reduce the incidence and severity of neurological damage caused by trauma, or the risk of such damage. Formulations, procedures and methods of the invention advantageously effect both neuroprotective actions to prevent or reduce secondary injuries, and neurotrophic actions to repair and restore cells and tissues affected by the trauma, and are especially useful in treating injury or trauma to nerve cells, to neural support cells and to neural support tissues.

13 Claims, No Drawings

(56) References Cited

U.S. PATENT DOCUMENTS

| | | | |
|---|---|---|---|
| 7,872,129 B2 | 1/2011 | Forster et al. | |
| 7,935,333 B2 | 5/2011 | During | |
| 10,201,569 B2 | 2/2019 | Henry | |
| 2002/0072509 A1* | 6/2002 | Stein | A61P 25/28 514/169 |
| 2003/0027817 A1 | 2/2003 | Tollefson | |
| 2003/0077564 A1 | 4/2003 | Brewer | |
| 2004/0132636 A1* | 7/2004 | Dooley | A61P 11/14 514/1 |
| 2005/0004106 A1 | 1/2005 | Romano | |
| 2007/0049565 A1 | 3/2007 | Gwag | |
| 2008/0107756 A1 | 5/2008 | Satow | |
| 2009/0203658 A1 | 8/2009 | Marx et al. | |
| 2010/0316678 A1 | 12/2010 | Goodchild | |
| 2011/0046090 A1 | 2/2011 | Barlow et al. | |
| 2011/0288059 A1 | 11/2011 | Marx et al. | |
| 2011/0301133 A1 | 12/2011 | Wu et al. | |
| 2014/0193523 A1 | 7/2014 | Henry | |
| 2014/0193526 A1 | 7/2014 | Henry | |
| 2014/0193528 A1 | 7/2014 | Henry | |
| 2014/0194394 A1 | 7/2014 | Henry | |
| 2014/0194397 A1 | 7/2014 | Henry | |

FOREIGN PATENT DOCUMENTS

| | | |
|---|---|---|
| WO | 2009089024 A1 | 7/2009 |
| WO | 2010077680 A2 | 7/2010 |
| WO | 20100107815 A1 | 9/2010 |
| WO | 2012112340 A2 | 8/2012 |
| WO | 2014107794 A2 | 7/2014 |
| WO | 2014108807 A2 | 7/2014 |
| WO | 2014108808 A2 | 7/2014 |
| WO | 2014108809 A2 | 7/2014 |
| WO | 2014140802 A2 | 9/2014 |

OTHER PUBLICATIONS

Freynhagen, R. et al., "Efficacy and Safety of Pregabalin in Treatment of Refactory Patients with Various Neuropathic Pain Entities in Clinical Routine", Int. J. Coin. Pract., 2007, 6212, pp. 1989-1996.

International Search Report and Written Opinion of WO2014/108808 dated Jul. 23, 2014.

Drug Information Online, Aprepitant Side Effects, May 15, 2012, http://www.drugs.com/sfx/aprepitant-side-effects.html, pp. 1-3.

International Search Report and Written Opinion of WO2014/140802 dated Oct. 8, 2014.

International Search Report and Written Opinion of WO2014/162195 dated Aug. 28, 2014.

Liu, Xishi et al, "Valproic Acid and Progestin Inhibit Lesion Growth and Reduce Hyperalgesia in Experimentally Induced Endometriosis in Rats", Journal of Obstetrics and Gynaecology Research, Jun. 2011.

Dableh, Liliane J. et al, "Progesterone Prevents Development of Neuropathic Pain in a Rat Model: Timing and Duration of Treatment are Critical", Journal of Pain Research, 2011:4, pp. 91-101.

Rampetsreiter, Matt et al., "Choosing Medications for Painful Diabetic Neuropathy", Podiatry Today, vol. 16, Issue 7, Jul. 2003.

Peng, Philip WH et al., "Use of Gabapentin for Perioperative Pain Control—A Meta-Analysis", Pain. Res. Manage, vol. 12, No. 2, 2007, pp. 85-92.

Mcvitamins, "Neuropathy (Nerve Damage) Caused by Trauma", www.mcvitamins.com/causes of neuropathy/trauma-caused-neuropathy.htm, (2016).

Ture, Hatic et al., "The Analgesic Effect of Gabapentin as a Prophylactic Anticonvulsant Drug on Postcraniotomy Pain: A Prospective Randomized Study", Anesthesia & Analgesia, Nov. 2009, vol. 109, Issue 5., p. 1625-31.

Cole, Jeffrey T. et al., "Craniotomy: True Sham for Traumatic Brain Injury, or a Sham of a Sham?", Journal of Neurotrauma, vol. 28.3, 2011, pp. 359-369.

Dahl, J.B. et al., "Protective Premedication: An Option with Gabapentin and Related Drugs?", Acta Anaesthesiologica Scandinavica, 2004, vol. 48, pp. 1130-1136.

International Search Report and Written Opinion of WO2014/107794 dated May 6, 2014.

* cited by examiner

PHARMACEUTICAL FORMULATIONS FOR THE TREATMENT AND PREVENTION OF TRAUMA-INDUCED NEUROPATHOLOGY AND NEURODEGENERATION

RELATED APPLICATION AND PRIORITY

This Utility Patent Application is a continuation of commonly owned U.S. Utility patent application Ser. No. 14/921,058, as filed on Oct. 23, 2015, and as entitled "Pharmaceutical Formulations for the Treatment and Prevention of Trauma-Induced Neuropathology and Neurodegeneration", which application is a continuation patent application of commonly owned U.S. Utility patent application Ser. No. 14/148,709, as filed on Jan. 6, 2014, and as entitled "Pharmaceutical Formulations for the Treatment and Prevention of Trauma-Induced Neuropathology and Neurodegeneration", which application claims the priority and benefit of commonly owned U.S. Provisional Patent Application Ser. No. 61/750,745, as filed 9 Jan. 2013, and as entitled "Formulations, Methods And Procedures For Reducing Or Preventing The Development Or The Risk Of Development Of Neuropathology As A Result Of Traumatic Injury," which utility and provisional patent applications are hereby incorporated by reference in their entirety into the present patent application. Also hereby incorporated by reference in their entireties are each of the references cited herein, as well as those cited in Utility patent application Ser. Nos. 14/148,709 and 14/921,058, and Provisional Patent Application Ser. No. 61/750,745.

FIELD OF THE INVENTION

The presently disclosed invention and many particular invention embodiments relate to multiple-component formulations, the use of such formulations, and to methods, procedures and combinations thereof to prevent or reduce, or to reduce the risk of, the damage that can otherwise lead to numerous types of neuropathology as a result of trauma.

SUMMARY OF THE INVENTION

Anticonvulsant/antiepileptic compounds suitable for use as components of invention embodiments include, but not exclusively, one or more from the group comprising gabapentin, pregabalin, barbiturates (such as phenobarbital, methylphenobarbital, metharbital, barbexaclone and other central nervous system depressants), benzodiazepines (such as clozepam, clonazepam, chlorazepate, diazepam, midazolam, lorazepam, and other hypnotic, anxiolytic, anticonvulsant, amnesic compounds), bromides (such as potassium bromide,) carbamates (such as felbamate, fluorofelbamate), carboxamides (such as carbamazepine, oxcarbazepeine, eslicarbazepine acetate), fatty acids (such as valproic acid, sodium valproate, divalproex sodium, vigabatrin, progabide, sec-butyl-propylacetamide), fructose derivatives (such as topiramate), hydantoins (such as ethotoin, phenytoin, mephenytoin, fosphentoin), oxazolidinediones (such as paramethadione, trimethadione, ethadione), propionates (such as beclamide), pyrimidinediones (such as primidone), pyrrolidines (such as rivaracetam, levetiracetam, seletracetam), succinimides (such as ethosuximide, phensuximide, mesuximide), sulfonamides (such as acetazolamide, sultiame, methazolamide, zonisamide), triazines (such as lamotrigine), ureas (such as pheneturide, phenacemide) and valproyamides (such as valpromide, valoctamide) and others known and unknown, as well as any homolog or derivative or compound acting on or through a receptor, an enzyme or other mechanism upon which an anticonvulsive/antiepileptic can act, as well as any compound acting on or through mechanisms that would modify or affect in any way pathways or processes affected by one or more anticonvulsant/antiepileptic compounds, as well as any related slow-release compound.

Neurosteroid/neuroactive steroid compounds suitable for use as components of invention embodiments include, but not exclusively, one or more from the group comprising progesterone, progesterone prodrugs, progesterone derivatives, progesterone analogs, and other progesterone compounds such as but not exclusive to medroxyprogesterone acetate, megestrol acetate, 17α-hydroxyprogesterone, 5α-dihydroxyprogesterone, 3α,5α-trihydroxyprogesterone, 14β-hydroxy progesterone, 17α-hydroxyprogesterone caproate, 16-methyl-17-benzoyl oxypregnen-4-en-3,20-dione, hydroxyprogesterone-3-O-carboxymethyloxime, 21-succinyloxy-6,19-epoxyprogesterone, 6,19-oxidoprogesterone, 17-p-bromophenylcarbamoyloxypregn-4-ene-3,20-dione, 17-phenyl carbamoyl-oxypregn-4-ene-3,20-dione, 4-pregnene-3,20-dione, 6,19-methanoprogesterone, 16,17-cyclohexano-4,5-dihydroprogesterone, nepapakistamine, vaganine D, Crinone, 18-oxo-18-vinylprogesterone, 16,17-cyclopropanoprogesterone, caproxyprogesterone, 21-hydroxy-6,19-oxidoprogesterone, 17-acetoxy-9-fluoro-6-methylprogesterone, ZK 136798, 3,17-dihydroxy-7-(4-methoxyphenyl)-androst-5-ene, 3,17-diacetate, progesterone-11HS-horseradish peroxidase, 21-hydroxy-11,19-oxidopregn-4-ene-3,20-dione, 21-hydroxy-6,19-oxidopregn-4-ene-3,20-dione, 4-cyanoprogesterone, 11,19-oxidoprogesterone, 6-fluoroprogesterone, 2-hydroxy-4-pregnene-3,20-dione, progesterone-3-(O-carboxymethyl oxime)-horseradish peroxidase, progesterone-11-hemisuccinyl-bovine serum albumin, pentarane B, pentarane A, progesterone 6-hemimaleate, progesterone 6-hemisuccinate, 7-(carboxyethylthio) progesterone, progesterone 3-(O-carboxymethyl)oxime-bovine serum albumin, 18-ethynylprogesterone, 18-vinylprogesterone, 6-methylprogesteron-17-pivalate, progesterone-11-bovine serum albumin, allylestriol, progesterone-3-ethanolimine, 3,20-dioxopregn-4-ene-18'-carboxaldehyde cyclic 18'-(1,2-ethandiylmercaptal), 18-ethylenedithioprogesterone, 17-acetoxy-6,16-dimethylene-4-pregnene-3,20-dione, 17-hydroxy-6-dehydroprogesterone, 2'-methyl-16,17-cyclohexaneprogesterone, 21,21-dichloroprogesterone, hydroxyprogesterone hemi succinate bovine serum albumin tetramethylrhodamine isothiocyanate, 11-progesteryl-2-carboxymethyltyramine-4-(10-methyl)acridinium-9-carboxylate, progesterone 12-succinyltyrosine methyl ester, progesterone 11-succinyltyrosine methyl ester, 11-progesteryl-2-succinoyltyramine-4-(10-methyl)acridinium-9-carboxylate, 2-hydroxymethyleneprogesterone, 2-cyanoprogesterone, 17-(phenylseleno)progesterone, 21-(phenyl seleno)progesterone and others known and unknown, and include other neurosteroids or neuroactive steroids such as, but not exclusive to prednisolone, methylprednisolone, alphaxolone, alphadolone, hydroxydone, minaxolone, ganaxolone, deoxycorticosterone, 3 alpha-hydroxy-5-alpha-pregnan-one (allopregnanolone), 3 alpha, 21-dihydroxy-5 alpha-pregnan-20-one (allotetrahydro), as well as metabolites of neurosteroids and neuroactive steroids, and including any corticoid, glucocorticoid, estrogen compound or any such compound acting on or through a progesterone, corticosteroid, glucocorticoid, estrogen or other neurosteroid receptor or through any other mechanism upon which progesterone, a corticosteroid, a glucocorticoid, an estrogen or other neurosteroid does or can act, as well as any homolog or derivative or compound acting on or through mechanisms that would modify, modulate or affect in any way pathways or processes affected by progesterone, estrogen or any neurosteroid, as well as any related slow-release compound.

NK-1 receptor antagonist compounds suitable for use as components of invention embodiments include, but not exclusively, any biologically active compound of one or more from the group comprising aprepitant, fosaprepitant, casopitant, maropitant, vestipitant, CP-99,994, CP-122,721, MK 869, LY 303870, RPR 67580, RPR 100893, L 758298, L 365260, L 733060, GR 205171, CGP 49823, CJ 11974, and others known and unknown, and any compound acting on or through the NK-1 receptor or any other mechanism that involves activation or involvement of the NK-1 receptor or its synthesis, and other chemical entities known and unknown, including any ligand or compound acting on or through an NK-1 receptor or other mechanism upon which substance P, an endogenous ligand for the NK-1 receptor, does or can act, as well as any compound acting on or through mechanisms that would modify or affect in any way pathways or processes affected by substance P or the NK-1 receptor, as well as any related slow-release compound. Further, in view of the evidence that some ligands and compounds can act through or by NK-2 or NK-3 receptors, any ligand or homolog or derivative or compound acting on or through an NK-1 or NK-2 or NK-3 receptor, including receptor isoforms, or related mechanism as well as any ligand that occupies, activates or deactivates these receptors, is included in the presently disclosed technology.

Lithium-related/lithium-containing compounds suitable for use as components of invention embodiments include, but not exclusively, any biologically active compound of one or more from the group comprising lithium citrate, lithium carbonate, lithium chloride, lithium bromatum and others known and unknown, as well as any compound acting on or through a lithium receptor or other mechanism upon which lithium does or can act, as well as any homolog or derivative or compound acting on or through mechanisms that would modify or affect in any way pathways or processes affected by lithium, as well as any related slow-release compound.

Numerous compounds can be administered to a subject in any combination or permutation of these classes of compound to practice this invention aimed to reduce or prevent the development or the risk of development of neuropathology as a result of traumatic injury to a subject by administering to a subject in need thereof a multiplicity of compounds by such combinations of any two, any three or any four compounds from the classes of compounds comprising anticonvulsants/antiepileptics, neurosteroids/neuroactive steroids, NK-1 receptor antagonists and lithium-related/lithium-containing compounds. These combinations of above said compounds can be given by various routes of administration to treat any injury or damage that has resulted, will result or may result from trauma, and that injury or damage can be to any nerve cell or nerve cells, to any neural support cell as described herein, or to any neural support tissue as described herein. Injury or damage can be to the brain, the brain stem, the cerebellum, the spinal cord, the enteric nervous system and the peripheral nervous system or any other nerve cell. A subject in need of invention embodiments can be an individual who is at risk of injury or damage, an individual who is about to experience an event that has the potential to cause traumatic damage or injury, or an individual who has experienced a trauma as described herein.

The presently disclosed technology includes formulations, methods and procedures aimed at reducing or preventing the development, or the risk of development, of neuropathology as a result of traumatic injury. Embodiments of the invention address unmet or unsolved medical needs including brain injury, central nervous system ischemia, spinal cord injury, enteric nervous system injury, peripheral nerve injury and any other injury that can include or affect nerve cells, neural support cells or neural support tissues. These unmet or unsolved medical needs share the commonness of the potential for life-long adverse health conditions or disability. They also share the commonness of the void in current medical interventions to reduce or prevent these adverse health conditions or disability.

These conditions also share similar, common or overlapping mechanisms of the secondary injury that develops following a primary injury or trauma, common mechanisms that trigger or lead to this secondary injury and common possible therapeutic targets for inhibiting or promoting the cascades of mechanisms triggered by a primary injury. As such mechanisms are triggered immediately by trauma while others downstream in the cascades of biochemical and metabolic pathways are engaged at different times following trauma, it is necessary to administer components of the formulation through the hours, days and in some cases the weeks following trauma, with immediate initiation of treatment of paramount importance for the preventive measures to arrest the degenerative cascades and to promote the restorative cascades, as well as continuation of practice according to need.

DETAILED DESCRIPTION OF THE INVENTION

In accordance with some of the objects of the invention, formulations for use in one or more treatments, procedures and methods to prevent the development, or the risk of development, of neuropathology and neurodegeneration sequelae associated with or caused by trauma or neurotrauma to a subject in need, or for the amelioration of the effects caused by trauma to a subject in need, are provided.

In one advantageous aspect, the present technology presents many embodiments of formulations comprising, or consisting essentially of, any two or any three or all four biologically active compounds in amounts that are pharmaceutically effective for each compound, respectively, when used in combination with the other biologically active compounds, the compounds being selected from a pharmaceutically effective amount of any two or any three or all four of A) at least one biologically active compound selected from the group comprising anticonvulsants and antiepileptics; B) at least one biologically active compound selected from the group comprising neurosteroids and neuroactive steroids; C) at least one biologically active compound selected from the group comprising NK-1 receptor antagonists; and D) at least one biologically active compound selected from the group comprising lithium-containing and lithium-related compounds.

As one of skill in the art will appreciate, many embodiments of the present formulations suitable for use in methods or procedures for treatment of such neuropathology and neurodegeneration sequelae associated with or caused by trauma or neurotrauma are within the scope and spirit of the present technology. Such formulations include, as examples, wherein the at least one anticonvulsant or antiepileptic agent is one or more from the group consisting of gabapentin, pregabalin, barbiturates (such as phenobarbital, methylphenobarbital, metharbital, barbexaclone and other central nervous system depressants), benzodiazepines (such as clozepam, clonazepam, chlorazepate, diazepam, midazolam, lorazepam, and other hypnotic, anxiolytic, anticonvulsant, amnesic compounds), bromides (such as potassium bromide), carbamates (such as felbamate, fluorofelbamate), carboxamides (such as carbamazepine, oxcarbazepine, eslicarbazepine acetate), fatty acids (such as valproic acid, sodium valproate, divalproex sodium, vigabatrin, progabide, sec-butyl-propylacetamide), fructose derivatives (such as topiramate), hydantoins (such as ethotoin, phenytoin, mephenytoin, fosphentoin), oxazolidinediones (such as paramethadione, trimethadione, ethadione), propionates (such as beclamide), pyrimidinediones (such as primidone), pyrrolidines (such as rivaracetam, levetiracetam, seletracetam), succinimides (such as ethosuximide, phensuximide, mesuximide), sulfonamides (such as acetazolamide, sultiame, methazolamide, zonisamide), triazines (such as lamotrigine), ureas (such as pheneturide, phenacemide) and valproyamides (such as valpromide, valoctamide) and others known and unknown, as well as any homolog or derivative or compound acting on or through a receptor, an enzyme or other mechanism upon which an anticonvulsive/antiepileptic can act, as well as any compound acting on or through mechanisms that would modify or affect in any way pathways or processes affected by one or more anticonvulsant/antiepileptic compounds, as well as any related slow-release compound.

In a similar advantageous combinatorial aspect, the present technology provides many embodiments of formulations comprising any two, or any three, or all four, biologically active compounds in amounts that are pharmaceutically effective for each compound, respectively, when used in combination with the other biologically active compounds, wherein the at least one neurosteroid or neuroactive steroid is one or more compounds selected from the group consisting of progesterone, progesterone prodrugs, progesterone derivatives, progesterone analogues, and other progesterone compounds such as but not exclusive to medroxyprogesterone acetate, megestrol acetate, 17alpha-hydroxyprogesterone, 5 alpha-dihydroxyprogesterone, 3 alpha, 5 alpha-trihydroxyprogesterone, 14b-hydroxy progesterone, 17alpha-hydroxyprogesterone caproate, 16-methyl-17-benzoyloxypregnen-4-en-3,20-dione, hydroxyprogesterone-3-O-carboxymethyloxime, 21-succinyloxy-6,19-epoxyprogesterone, 6,19-oxidoprogesterone, 17-p-bromopheny-1carbamoyloxy-pregn-4-ene-3,20-dione, 17-phenylcarbamoyl-oxypregn-4-ene-3,20-dione, 4-pregnene-3,20-dione, 6,19-methanoprogesterone, 16,17-cyclohexano-4,5-dihydroprogesterone, nepapakistamine, vaganine D, Crinone, 18-oxo-18-vinylprogesterone, 16,17-cyclopropanoprogesterone, caproxyprogesterone, 21-hydroxy-6,19-oxidoprogesterone, 17-acetoxy-9-fluoro-6-methylprogesterone, ZK 136798, 3,17-dihydroxy-7-(4-methoxyphenyl)-androst-5-ene, 3,17-diacetate, progesterone-11HS-horseradish peroxidase, 21-hydroxy-11,19-oxidopregn-4-ene-3,20-dione, 21-hydroxy-6,19-oxidopregn-4-ene-3,20-dione, 4-cyano-progesterone, 11,19-oxidoprogesterone, 6-fluoroprogesterone, 2-hydroxy-4-pregnene-3,20-dione, progesterone-3-(O-carboxymethyl oxime)-horseradish peroxidase, progesterone-11-hemisuccinyl-bovine serum albumin, pentarane B, pentarane A, progesterone 6-hemimaleate, progesterone 6-hemisuccinate, 7-(carboxyethylthio)progesterone, progesterone 3-(O-carboxy-methyl)oxime-bovine serum albumin, 18-ethynylprogesterone, 18-vinylprogesterone, 6-methylprogesteron-17-pivalate, progesterone-11-bovine serum albumin, allylestriol, progesterone-3-ethanolimine, 3,20-dioxopregn-4-ene-18'-carboxaldehyde cyclic 18'-(1,2-ethandiylmercaptal), 18-ethylenedithioprogesterone, 17-ac-etoxy-6,16-dimethylene-4-pregnene-3,20-dione, 17-hydroxy-6-dehydroprogesterone, 2'-methyl-16,17-cyclohexaneprogesterone, 21,21-dichloroprogesterone, hydroxyprogesterone hemisuccinate bovine serum albumintetramethylrhodamine isothiocyanate, 11-progesteryl-2-carboxymethyl-tyramine-4-(10-methyl)acridinium-9-carboxylate, progesterone 12-succinyltyrosine methyl ester, progesterone 11-succinyltyrosine methyl ester, 11-progesteryl-2-succinoyltyramine-4-(10-methyl)acridinium-9-carboxylate, 2-hydroxymethyleneprogesterone, 2-cyanoprogesterone, 17-(phenylseleno)progesterone, 21-(phenylseleno)progesterone and others known and unknown, and include other neurosteroids or neuroactive steroids such as, but not exclusive to neuroactive progestagens (including but not limited to pregnenolone (3beta-hydroxypregn-5-en-20-one), 17α-hydroxy-pregnenolone, progesterone, 17α-hydroxyprogesterone, dehydroepiandrosterone, androstenedione, deoxycorticosterone, 11-deoxycortisol, 3 alpha-hydroxy-5 alpha-pregnan-20-one (allopregnanolone), 3 alpha,21-dihydroxy-5 alpha-pregnan-20-one allotetrahydroDOC)), neuroactive androgens (including but not limited to androstenedione (the precursor of 3alpha,5alpha-A, or androsterone), androsterone (5alpha-androstan-3 alpha-ol-17-one; 3alpha,5alpha-A), 5alpha-dihydrotestosterone (5alpha-DHT) and its metabolite 5alpha-androstane-3 alpha,17b eta-diol (3 alpha,5 alpha-Adiol), 3α,17β-dihydroxy-5α-androstane, 3α-hydroxy-5α-androstan-17-one, 3α-hydroxy-5β-androstan-17-one, androst-5-ene-3β,17β-diol, 3β,17α-dihydroxy-pregn-5-en-20-one (17α-hydroxy-pregnenolone), 3β-hydroxy-androst-5-en-17-one (dehydroepiandrosterone, DHEA), testosterone, androst-4-ene-3,17-dione (androstenedione), neuroactive estrogens (including but not limited to estradiol, 17β-estradiol (βE2), 17α-estradiol (αE2), estrone (E1) and estriol (E3), and phytoestrogens), neuroactive glucocorticoids (including but not limited to prednisolone), other neuroactive steroids metabolically downstream from these principal neuroactive steroids including but not limited to allopregnanolone, allotetrahydrodeoxycorticosterone (THDOC), and dehydroepiandrosterone (DHEA), additional neuroactive steroids including other derivatives such as estradiol benzoate, neurosteroids and neuroactive steroids including, but not limited to, prednisolone, methylprednisolone, alphaxalone, alphadolone, hydroxydone, minaxolone, ganaxolone, deoxycorticosterone, 3 alpha-hydroxy-5-alpha-pregnan-one (allopregnanolone), 3 alpha,21-dihydroxy-5 alpha-pregnan-20-one (allotetrahydro), as well as metabolites of neurosteroids and neuroactive steroids, and including any corticoid, glucocorticoid, estrogen, estrogen compound, androgen or androgen compound or any such compound acting on or through a progesterone, corticosteroid, glucocorticoid, estrogen, androgen or other neurosteroid or neuroactive steroid receptor or through any other mechanism upon which progesterone, a corticosteroid, a glucocorticoid, an estrogen or other neurosteroid or neuroactive steroid does or can act, as well as any homolog or derivative or compound acting on or through mechanisms that would modify, modulate or affect in any way pathways or processes affected by progesterone, estrogen or any neurosteroid or neuroactive steroid, as well as any related slow-release compound.

In yet another advantageous combinatorial aspect, the present technology also provides many embodiments of formulations comprising any two, or any three, or all four, biologically active compounds in amounts that are pharmaceutically effective for each compound, respectively, when used in combination with the other biologically active compounds, wherein the at least one NK-1 receptor antagonist is one or more from the group consisting of aprepitant, fosaprepitant, casopitant, maropitant, vestipitant, CP-99,994, CP-122,721, MK 869, LY 303870, RPR 67580, RPR 100893, L 758298, L 365260, L 733060, GR 205171, CGP 49823, CJ 11974, and others known and unknown, and any compound acting on or through the NK-1 receptor or any other mechanism that involves activation or involvement of the NK-1 receptor or its synthesis, and other chemical entities known and unknown, including any ligand or compound acting on or through an NK-1 receptor or other mechanism upon which substance P, an endogenous ligand for the NK-1 receptor, does or can act, as well as any compound acting on or through mechanisms that would modify or affect in any way pathways or processes affected by substance P or the NK-1 receptor, as well as any related slow-release compound. Further, in view of the evidence that some ligands and compounds can act through or by NK-2 or NK-3 receptors, any ligand or homolog or derivative or compound acting on or through an NK-1 or NK-2 or NK-3 receptor, including receptor isoforms, or related mechanism as well as any ligand that occupies, activates or deactivates these receptors, is included in the presently disclosed technology.

In yet an additional advantageous and combinatorial aspect, the many embodiments of the present technology include many embodiments of formulations comprising any two or any three or all four biologically active compounds in amounts that are pharmaceutically effective for each compound, respectively, when used in combination with the other biologically active compounds, wherein the at least one lithium-containing/lithium-related agent is one or more from the group consisting of lithium carbonate, lithium citrate, lithium chloride, lithium bromatum and others known and unknown, as well as any compound acting on or through a lithium receptor or other mechanism upon which lithium does or can act, as well as any homolog or derivative or compound acting on or through mechanisms that would modify or affect in any way pathways or processes affected by lithium, as well as any related slow-release compound.

Examples of the many embodiments of formulations, methods and procedures of the present technology are many. These include wherein the formulation consists of any two, or any three, or all four, of the anticonvulsants or antiepileptics, the neurosteroids or neuroactive steroids, the NK-1 receptor antagonists and the lithium-containing or lithium-related compounds, and wherein the formulation is formulated, or adapted and arranged, for administration within 12 hours after the trauma.

Such examples also include wherein the formulation consists essentially of any two, or any three, or all four, of the anticonvulsants or antiepileptics, the neurosteroids or neuroactive steroids, the NK-1 receptor antagonists and the lithium-containing or lithium-related compounds, and wherein the formulation is formulated, or adapted and arranged, to be first administered to a mammal in need thereof, within 24 hours after the trauma.

In a similar aspect, the present technology includes formulations consisting essentially of any two, or any three, or all four, of the anticonvulsants or antiepileptics, the neurosteroids or neuroactive steroids, the NK-1 receptor antagonists and the lithium-containing or lithium-related agents, and is formulated, or adapted and arranged, to be first administered as a prophylactic measure within 90 minutes before an expected or potential trauma, and wherein the formulation consists essentially of any two, or any three, or all four, of the anticonvulsant or antiepileptic, the neurosteroid or neuroactive steroid, the NK-1 receptor antagonist and the lithium-containing or lithium-related agent are formulated, or adapted and arranged, for administration within 24 hours of the trauma.

The present technology also includes formulations consisting essentially of combinations wherein the anticonvulsants or antiepileptics, the neurosteroids or neuroactive steroids and the NK-1 receptor antagonists are formulated for administration as a preventive measure within 90 minutes before a possible trauma.

Moreover, embodiments of the present technology include wherein the formulation consists of any two or any three or all four of the anticonvulsant or antiepileptic, the neurosteroid or neuroactive steroid, the NK-1 receptor antagonist and the lithium-containing or lithium-related agent, and is formulated for administration as a precautionary measure within 90 minutes before a possible trauma.

Formulations of the present invention include also wherein the formulation comprises a single dosage unit, wherein the formulation is adapted and arranged for administration a plurality of times, such as in some type or types of sequences. These include wherein the formulation is adapted and arranged for administration in one or more dosage units per day, and wherein they are formulated for administration as one or more of tablets, capsules, pills, lozenges or as one or more ingestible or injectable solutions.

Consonant with the numerous embodiments of the invention are formulations adapted and arranged, or provided, as examples, for administration via an oral, buccal, mucosal, parenteral, rectal, sub-cutaneous, transdermal, intravenous, intrathecal, intravaginal, nasal, nasal inhalation, pulmonary inhalation, iontophoresis through the skin, iontophoresis through mucosal or buccal membranes, dermal patch, epidural, intracranial, intrapharyngeal, sublingual, intra-articular, intramuscular or a subcutaneous route. Preferable subjects of the present technology include animals such as mammals, and more preferably humans.

As yet another advantage, the present formulations can be provided in one or more such forms adapted and arranged to be administered to, given to, or taken by, a subject, and may include other ingredients or substances such as excipients, buffers, penetration enhancers, stabilizers, absorption enhancers and carriers.

Also consonant with the present formulations are those wherein one or more of the compounds is in the form of one or more of salts, prodrugs, hydrates, derivatives or metabolites of the compound itself, analogues, homologues, compounds acting on or through mechanisms that compounds can act on or through or compounds that modify, modulate or affect in any way pathways or processes affected by compounds or formulations of the invention.

As one of skill in the art will comprehend, the present technology includes numerous combinations, variations and permutations of the many formulations provided within the spirit and scope of the present description. Examples of embodiments of the present formulations include wherein the at least one anticonvulsant is gabapentin, in a form adapted and arranged for administration to a mammal in need thereof, wherein the at least one anticonvulsant is pregabalin, in a form adapted and arranged for administration to a mammal in need thereof, and wherein the at least one anticonvulsant is valproic acid, in a form adapted and arranged for administration to a mammal in need thereof.

Exemplary formulation dosage ranges of the present technology include, as examples, wherein the gabapentin is provided in a range of from 5.0 to 9,600 mg, wherein the pregabalin is provided in a range of from 0.5 to 2,400 mg, wherein the valproic acid is provided in a range of from 25 to 4,800 mg.

Examples of embodiments of the present formulations include also wherein the at least one neurosteroid is progesterone, in a form adapted and arranged for administration to a mammal in need thereof, wherein the at least one neurosteroid is methylprednisolone, in a form adapted and arranged for administration to a mammal in need thereof, and wherein the at least one neurosteroid is medroxyprogesterone acetate, in a form adapted and arranged for administration to a mammal in need thereof.

Exemplary formulation dosage ranges of the present technology include wherein the progesterone is provided in a range of from 0.05 to 1,200 mg, the methylprednisolone, is provided in a range of from 0.02 to 500 mg, wherein the medroxyprogesterone acetate, is provided in a range of from 0.001 to 400 mg. Examples of embodiments of the present formulations include also wherein the at least one NK-1 receptor antagonist is aprepitant, in a form adapted and arranged for administration to a mammal in need thereof, wherein the at least one NK-1 receptor antagonist is vestipitant, in a form adapted and arranged for administration to a mammal in need thereof wherein the at least one NK-1 receptor antagonist is casopitant, in a form adapted and arranged for administration to a mammal in need thereof.

Dosage ranges of the individual two, or three or four components of the present formulations include any which are effective, and especially wherein the aprepitant, is provided in a range of from 0.05 to 750 mg, wherein the vestipitant, is provided in a range of from 0.001 to 200 mg, and wherein the casopitant, is provided in a range of from 0.005 to 1,000 mg.

With respect to lithium-containing variations of the present invention, the present formulations include wherein the at least one lithium-containing compound is lithium carbonate, in a form adapted and arranged for administration to a mammal in need thereof; wherein the at least one lithium-containing compound is lithium citrate, in a form adapted and arranged for administration to a mammal in need thereof, and wherein the at least one lithium-containing compound is lithium chloride, in a form adapted and arranged for administration to a mammal in need thereof.

With respect to exemplary dosage ranges, embodiments of the present technology include also wherein the lithium carbonate, is provided in a range of from 0.5 to 3,600 mg, wherein the lithium citrate, is provided in a range of from 0.01 to 2,400 mg, and wherein the lithium chloride, is provided in a range of from 3.0 to 3,600 mg.

The present technology includes also wherein embodiments of the present formulations are adapted and arranged to treat one or more changes in cellular or tissue structure, function or health, occurring in one or more of the central nervous system, including the brain, the brainstem, the cerebellum and the spinal cord, and the periphery, including the enteric nervous system and the peripheral nervous system, and also wherein they are adapted and arranged to treat one or more selected from the group comprising neuropathy, neuropathology, neurodegeneration and the effects of trauma, and those governed by a balance of neurotrophic/neuroprotective and neurodegenerative mechanisms.

The present technology includes also wherein embodiments of the present formulations are adapted and arranged to treat one or more changes governed by neurotrophic and regenerative mechanisms that repair or regenerate nerve cells, neural support cells or neural support tissues. In a similar manner, the present technology includes also wherein embodiments of the present formulations are adapted and arranged to treat one or more changes governed by neurodegenerative mechanisms that lead to secondary injury, neuropathology and neurodegeneration, and cell death.

The presently disclosed technology also includes wherein embodiments of the present formulations are adapted and arranged to treat neuroprotective mechanisms to prevent or ameliorate neuropathology and neurodegeneration caused by or resulting from trauma.

In accordance with the broad applicability of the present formulations, methods and procedures, the present formulations can also be adapted and arranged to treat one or more selected from the group comprising physical trauma, chemical trauma, metabolic trauma, medically-related trauma and other trauma, where injury or damage is to at least one nerve, at least one nerve cell, at least one neural support cell or at least one neural support tissue, whether in the central nervous system or in the periphery, and can also be adapted and arranged to treat one or more from the group comprising brain changes resulting short-, medium- or long-term from trauma, including Alzheimer's disease, Parkinson's disease and other disorders where brain trauma is a risk factor.

Similarly, formulations of the invention can be adapted and arranged to treat spinal cord trauma comprising one or more from the group comprising compression, vertebral collapse, cutting wounds, puncture wounds, crush wounds, surgical or medical intervention, and ischemia resulting from loss of blood, insufficient circulation from stoppage or slowing of the heart, or surgical interruption of the blood supply to the spinal cord.

Also, formulations of the invention also can be adapted and arranged to treat brain, brainstem and cerebellum trauma including one or more from the group comprising brain injury, ischemia of the central nervous system, physical trauma, chemical trauma, metabolic trauma, trauma from surgical or medical intervention or procedure and other trauma.

As one of skill in the art will appreciate, formulations of the invention can be adapted and arranged to treat enteric nervous system trauma including injury to one or more from the group comprising neurons, progenitor cells, glial cells and interstitial cells of Cajal, cells of Auerbach's myenteric plexus and Meissner's submucosal plexus, as well as neural support cells and neural support tissues, including luminal, lamina propria and muscularis mucosal cells, as well as endothelial cells of the vasculature.

Similarly, formulations of the invention can be adapted and arranged to treat peripheral nerve trauma including one or more from the group comprising sensory nerves, motor nerves, autonomic nerves, nerve cells, neural support cells, such as Schwann cells, myelin cells, satellite cells, as well as neural support tissues such as the vasculature. Other targets for the present formulations include those adapted and arranged to treat following trauma as an emergency treatment of trauma as would be in the case of unanticipated or accident-related trauma, taken as soon after trauma as possible that may prevent the development of neuropathology and neurodegeneration or the risk of development of neuropathology and neurodegeneration including such conditions as motor vehicle accidents, battlefield injuries, sports injuries, toxic chemical spill and the like, where evidence informs that there is a risk of damage to brain, spinal cord or peripheral nerve. Emergency treatment to prevent secondary injury, neuropathology and neurodegeneration is different from emergency treatment of trauma, where immediate steps are taken to prevent further injury, to stop bleeding, to stabilize the victim and to take life-saving steps.

The present formulations, methods and procedures can also be adapted and arranged to treat before trauma as would be in the case of anticipated, potential or purposeful trauma, taken as a pre-exposure prophylaxis measure to reduce the risk of neuropathology in individuals who are about to undergo procedures where there is a risk of trauma, including such conditions as surgery, chemotherapy, radiation therapy and the like, where evidence informs that there is a risk of damage to brain, brain stem, cerebellum, spinal cord, peripheral nerve and/or enteric nerve cells, and wherein prophylaxis treatment for trauma is different from pre- and post-surgical care, where steps are taken to ensure the patient's comfort and rapid recovery from the immediate condition.

Also advantageously, the present formulations, methods and procedures can also be adapted and arranged to anticipatorily treat before as a precaution in case of an unanticipated or accident-related trauma that may occur, as a pre-exposure precautionary measure taken to reduce the risk of neuropathology in individuals who are about to enter into a situation or condition where there is a great likelihood of trauma, including such conditions as a dangerous military or law enforcement operation or situation, an impending or underway bioterrorism or other attack where neurotoxic chemicals or other agents have been or may have been released.

In a similar manner, the present formulations can be adapted and arranged to treat any damage, wound, insult, cut, laceration, concussion, lesion, abrasion, contusion, shock, strain, abrupt acceleration, abrupt deceleration, explosion, percussion, metabolic event that causes, results in, brings about, triggers or leads to or can trigger or can lead to secondary injury or damage or change in structure or change in phenotype or change in gene expression or loss of function or altered function or cell death of a nerve cell, a neural support cell or a neural support tissue, as well as to treat physical trauma including vehicle accidents, workplace accidents, sports accidents, falls, burns, radiation, battlefield injuries, concussive injuries, blast injuries, injuries from landmines, injuries from improvised explosive devices, penetrating injuries, non-penetrating injuries or the result of any traumatic event that can injure, damage, modify, kill or otherwise change the phenotype, gene expression function of a nerve cell, a neural support cell or a neural support tissue.

In addition, the present technology can be adapted and arranged to treat chemical trauma including alcohol overdose, drug abuse, stimulant drugs, carbon dioxide poisoning, lead poisoning, copper poisoning, acrylamide and related chemicals, overexposure to certain environmental chemicals such as copper or natural hazards such as insect and other animal venom toxins, herbicides, insecticides, industrial toxic chemicals, bioterrorism chemicals and other chemicals that can injure, damage, modify, kill or otherwise change the phenotype, gene expression function of a nerve cell, a neural support cell or a neural support tissue.

Thus, the many embodiments of the invention are adaptable and arrangeable to treat metabolic trauma including, as examples, hypoxia, ischemia, hypoxia, multiple sclerosis, shingles, diabetes, stroke, epileptic or other seizure, post-polio syndrome, HIV/AIDS peripheral neuropathy, subacute posttraumatic myelopathy, and other effects, syndromes and conditions following a type of trauma to the body that can injure, damage, modify, kill or otherwise change the phenotype, gene expression function of a nerve cell, a neural support cell or a neural support tissue.

Other exemplary applications of the present technology include those adapted and arranged to treat trauma resulting from medical treatment or medical procedure trauma including injections, surgery, amputation, implantation, laparoscopy, chemotherapy (for example but not exclusively with methotrexate, cisplatin, cytosine arabinose, carmustine, thiotepa among others), radiation therapy, immunosuppressants (for example tacrolimus) and the like, or during a medical procedure that can reduce or impede the blood supply for any period of time and the like.

Trauma from surgery includes, as examples, laparoscopy, amputation, mastectomy, cesarean section, cardiac surgery, hernia repair, cholecystectomy, joint replacement, thoracotomy, reparative surgery or any case, condition or situation where there is or might be detectable or undetectable cut, wound, injury or damage to nerves, nerve cells, neural support cells or neural support tissues that can injure, damage, modify, kill or otherwise change the phenotype, gene expression function of a nerve cell, a neural support cell or a neural support tissue, as well as to treat trauma including radiation, burns, hypoxia, cold, heat or other trauma that can injure, damage, modify, kill or otherwise change the phenotype, gene expression function of a nerve cell, a neural support cell or a neural support tissue, and to treat any damage or injury to a cell that is required for or promotes or facilitates the normal function, health, survival, phenotype, gene expression and function of nerve cells including glial cells, microglia, myelin cells, satellite cells, astroglia, oligodendrocytes, Schwann cells, satellite cells, interstitial cells of Cajal and vascular endothelial cells, to treat any damage or injury to a tissue that supports or is required for or promotes or facilitates the normal function, health, survival, phenotype, gene expression, survival or function of nerve cells and neural support cells and includes the vasculature and microvasculature to nerve cells and neural support cells in the central nervous system and in the periphery, and to treat any neurotrophic mechanism or neurotrophic effect or neurotrophic action that encompass therapeutic strategies intended to promote, facilitate or augment survival, health, function, recovery, proliferation, differentiation, growth, or regeneration of one or more cells or tissues, and includes any biochemical, cellular, tissue or metabolic process that is activated by the traumatic event or by the direct tissue damage from that event and that leads to or can lead to restoration, recovery or repair of nerves, nerve cells, neural support cells or neural support tissue or that protects or restores health of nerves, nerve cells, neural support cells or neural support tissues.

SCOPE OF THE INVENTION

The foregoing description sets forth various embodiments of formulations, methods, procedures and practices for reducing or preventing the development, or the risk of development, of neuropathology as a result of traumatic injury. Insofar as such formulations, methods, procedures and practices contain one or more functions or operations, it will be understood by those within the art that each formulation, method, procedure and practice can be implemented, individually or collectively, within a wide range of many combinations without undue experimentation.

A person having ordinary skill in the art will recognize that, in one significant aspect, the herein described formulations (e.g., any combination of any two, any three or all four of gabapentin, progesterone, aprepitant and lithium), methods, and procedures and practices, and the discussion accompanying them, are used as examples for the sake of conceptual clarity and that various methods, procedures and practices are within the skill of those in the art. Consequently, as used herein, the specific exemplars set forth and the accompanying discussion are intended to be representative of their more general classes. In general, use of any specific exemplar herein is also intended to be representative of its class, and the non-inclusion of such specific formulation components (e.g., gabapentin, progesterone, aprepitant and lithium), methods, and procedures and practices herein should not be taken as indicating that limitation is desired.

It is generally contemplated that the formulations according to the inventive subject matter will be formulated for administration to a mammal, and especially to a human, having a condition that is responsive to the administration of such a formulation. Therefore, where contemplated formulation compounds are administered in a pharmacological composition, it is understood that contemplated compounds can be formulated in admixture with pharmaceutically acceptable carriers. As an example but not exclusively, contemplated compounds can be administered orally as pharmacologically acceptable salts, or intravenously in a physiological saline solution (e.g., buffered to a pH of about 7.2 to 7.5). Conventional buffers such as phosphates, bicarbonates or citrates can be used for this purpose. Of course, one of ordinary skill in the art may modify the formulations within the teachings of the present disclosure to provide numerous formulations for a particular route of administration.

In particular, contemplated compounds may be modified to render them more soluble in water or other vehicle that, for example, may be easily accomplished with minor modifications (e.g. salt formulation, esterification, etc.) that are well within the ordinary skill in the art. It is also well within the ordinary skill of the art to modify the route of administration and dosage regimen of a particular compound or formulation in order to manage the pharmacokinetics of the present compounds for maximum beneficial effect in a patient or subject.

Also in particular, contemplated compounds may be prepared for delivery in tablet, capsule, pill or solution form, including any form that can deliver a controlled release of these compounds.

Similarly, it should be appreciated that while some claims recite components of formulations of invention embodiments, one of skill in the art will comprehend that other constituents, while pharmacologically inactive or inert in the context of the presently disclosed technology, might be a part of the formulation. Such inactive constituents include, as examples, excipients, binders, coatings, absorption enhancers, penetration enhancers, transport enhancers, stabilizers, chelators, buffers, carriers, clearance modifiers, emulsifying agents, antioxidants, preservatives, sugars, salts, cellulose, dyes, flavoring agents and any other inactive ingredients that are considered generally recognized as safe.

In certain pharmaceutical dosage forms, prodrug and derivative forms of contemplated compounds may be formed for various purposes, including reduction of toxicity, increasing the organ or target cell specificity, etc. Among various prodrug and derivative forms, acylated (acetylated or other) derivatives, pyridine esters and various salt forms of the present compounds may be advantageous. One of ordinary skill in the art will recognize how to readily modify the present compounds to prodrug and other forms to facilitate delivery of active compounds to a target site within the host organism or patient. One of ordinary skill in the art will also take advantage of favorable pharmacokinetic parameters of the prodrug and other forms, where applicable, in delivering the present compounds to a targeted site within the host organism, subject or patient to maximize the intended effect of the formulation.

Similarly, it should be appreciated that contemplated compounds may also be metabolized to their biologically active form (e.g., via hydroxylation, glycolsylation, oxidation etc.), and all metabolites of the compounds herein are therefore specifically contemplated. In addition, contemplated compounds (and combinations thereof) may be administered in combination with yet further antiviral and/or antibacterial agents. Suitable additional drugs therefore include but are not limited to various antibiotics (e.g., beta-lactam antibiotics, tetracycline antibiotics, oxazine antibiotics, etc.), various antiviral compounds (e.g., polymerase inhibitors), and/or compounds that stimulate the immune system.

With the presently disclosed technology described in detail herein, it is to be understood that the invention is not limited to the particular embodiments described, as such may, of course, vary. It is also to be understood that the terminology used herein is for the purpose of describing particular embodiments, and is not intended to be limiting, since the scope of the presently disclosed technology will be limited only by the appended claims or by a fair reading of the application as a whole.

Where a range of values is provided, it is understood that each intervening value, to the tenth of the unit of the lower limit unless the context clearly dictates otherwise, between the upper and lower limit of that range and any other stated or intervening value in that stated range is encompassed within embodiments of the invention. The upper and lower limits of these smaller ranges may independently be included in the smaller ranges is also encompassed within embodiments of the invention, subject to any specifically excluded limit in the stated range. Where the stated range includes one or both of the limits, ranges excluding either or both of those included limits are also included in embodiments of the invention.

Unless defined otherwise, all technical and scientific terms used herein have the same meaning as commonly understood by one of ordinary skill in the art to which embodiments of this invention belongs. Although any methods and materials similar or equivalent to those described herein can also be used in the practice or testing of the presently disclosed technology, a limited number of the exemplary methods and materials are described herein.

All publications mentioned herein are hereby incorporated by reference to disclose and describe the methods and/or materials in connection with which the publications are cited, as well as the general background for the inventive subject matter disclosed herein. The publications discussed herein are provided solely for their disclosure prior to the filing date of the present application. Nothing herein is to be construed as an admission that the presently disclosed technology is not entitled to antedate such publication by virtue of prior invention. Further, the dates of publication provided might be different from the actual publication dates, which may need to be independently confirmed.

The inventive technology described herein sometimes illustrates different components contained within, or connected with, different other components. It is to be understood that such descriptions or subject matter are merely exemplary, and that in fact many other descriptions, examples, methods, procedures and practices can be implemented which achieve the same functionality. In a conceptual sense, any arrangement of components to achieve the same functionality is effectively "associated" or "coupled" such that the desired functionality is achieved. Hence, any two or more methods, procedures or practices herein combined to achieve a particular functionality can be seen as "associated with" each other such that the desired functionality is achieved, irrespective of condition, event, injury, damage or pathology components. Likewise, any two or more components so associated can also be viewed as being "operably connected", or "operably coupled", to each other to achieve the desired functionality, and any two or more components capable of being so associated can also be viewed as being "operably couplable", to each other to achieve the desired functionality. Specific examples of operably couplable include but are not limited to, practices of embodiments of the invention required under different conditions, practices of embodiments of invention requiring different routes or methods of administration, practices of embodiments of invention requiring repeated administration for varying periods of time or logically interacting or logically interactable components to achieve the desired functionality.

In a general sense, those skilled in the art will recognize that the various aspects described herein which could be implemented, individually or collectively, by a wide range of methods, procedures or practices, or any combination thereof, can be viewed as being composed of various types of "formulation." Consequently, as used herein "formulation" includes, but is not limited to, two compounds selected from gabapentin, progesterone, aprepitant and lithium, three compounds selected from gabapentin, progesterone, aprepitant and lithium or all four compounds selected from gabapentin, progesterone, aprepitant and lithium. Those having skill in the art will recognize that the subject matter described herein may be implemented in a method, procedure or practice as described herein, or some combination thereof.

As examples, the formulations, methods, procedures or practices of certain embodiments of the invention include many combinations and permutations thereof with respect to the nature of the individual formulations, and their relative methods, procedures or practices, can vary in operation by the relative methods, procedures or practices.

While particular aspects of the present subject matter described herein have been shown and described, it will be apparent to those skilled in the art that, based upon the embodiments herein, changes and modifications may be made without departing from the subject matter described herein and its broader aspects and, therefore, the appended claims are to encompass within their scope all such changes and modifications as are within the true spirit and scope of the subject matter described herein.

Those skilled in the art will recognize that it is common within the art to describe methods, procedures or practices in the fashion set forth herein, and thereafter use standard practices to integrate such described methods, processes or procedures to reduce or prevent the development or the risk of development of neuropathology as a result of traumatic injury. That is, at least a portion of the methods, procedures or practices described herein can be integrated into reducing or preventing the development or the risk of development of neuropathology as a result of traumatic injury via a reasonable amount of experimentation. Those having skill in the art will recognize that typical methods, procedures or practices generally include those described herein. A typical method, procedure or practice may be implemented utilizing any suitable commercially available instrument, tool or device, such as any typically found in a medical facility or health delivery context or venue, and available to those typically familiar with methods, procedures or practices generally applied by those skilled in the art.

With respect to the use of substantially any plural or singular terms herein, those having skill in the art can translate from the plural to the singular or from the singular to the plural as is appropriate to the context or application. The various singular/plural permutations are not expressly set forth herein for sake of clarity.

Furthermore, it is to be understood that the invention is defined by the appended claims, and by the many claims that could be supported by the present specification. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" or "an" should typically be interpreted to mean "at least one" or "one or more"); the same holds true for the use of definite articles used to introduce claim recitations.

It will be further understood by those within the art that virtually any disjunctive word or phrase presenting two or more alternative terms, whether in the description, claims, or practices, should be understood to contemplate the possibilities of including one of the terms, either of the terms, or both terms. It is also to be understood that the terminology employed in the Detailed Description sections of this application is for the purpose of describing particular embodiments. It is also contemplated that any optional feature of the inventive variations described herein may be set forth and claimed independently, or in combination with any one or more of the features described herein. Moreover, in interpreting the disclosure, all terms should be interpreted in the broadest possible manner consistent with the context of the disclosed technology. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

Thus, many specific compositions, procedures and methods of the present "Pharmaceutical Formulations For The Treatment And Prevention Of Trauma-Induced Neuropathology And Neurodegeneration" have been disclosed and exemplified. It should be apparent, however, to those skilled in the art that many more modifications besides those already described are possible without departing from the inventive concepts herein, or from the spirit of the invention. The inventive subject matter, therefore, is not to be restricted except in the spirit of the disclosure.

To assist in understanding the numerous embodiments of the invention, Table 1 provides some examples of dose ranges of drug categories for some particular embodiments of the invention. As such, Table 1 illustrates both the components of the 2-component, 3-component, and 4-component formulation of the invention, and the numerous unspecified formulations, which also fall within the spirit and scope of the invention.

TABLE 1

Dose Ranges of Drug Categories For Some Particular Embodiments of The Invention

| Drug category | Exemplary Compound | Acceptable Range (mg) | Preferable Range (mg) | More Preferable Range (mg) | Most Preferable Range (mg) |
|---|---|---|---|---|---|
| A/A | Gabapentin | 5-9,600 | 50-4,800 | 100-2,400 | 200-600 |
| A/A | Pregabalin | 0.5-2,400 | 15-1,200 | 25-600 | 50-150 |
| A/A | Valproic acid | 25-8,400 | 250-4,200 | 750-3,750 | 1,000-3,000 |
| N/N | Progesterone | 0.05-1,200 | 5-600 | 40-450 | 100-305 |
| N/N | Methylprednisolone sodium succinate | 0.02-500 | 2-250 | 10-80 | 15-45 |
| N/N | Medroxyprogesterone acetate | 0.001-400 | 0.5-200 | 1-50 | 2.5-7.5 |
| N/K | Aprepitant | 0.05-750 | 5-375 | 20-250 | 40-120 |
| N/K | Vestipitant | 0.001-200 | 1-100 | 1-60 | 5-15 |
| N/K | Casopitant | 0.005-1,000 | 0.5-500 | 10-300 | 50-150 |
| L/L | Lithium carbonate | 0.5-3,600 | 30-1,800 | 100-900 | 200-600 |
| L/L | Lithium citrate | 0.01-2,400 | 10-1,200 | 50-900 | 200-600 |
| L/L | Lithium chloride | 3-3,600 | 30-1,800 | 100-900 | 20600 |

The invention claimed is:

1. A method for reducing the incidence or severity of secondary injury to neurons, neural support cells and/or neural support tissues caused by trauma to a subject, consisting of administering to the subject in need thereof effective amounts of the following active agents:
    (A) gabapentin;
    (B) progesterone; and
    (C) optionally, lithium chloride,
    wherein the trauma is a physical trauma that causes secondary injury to neurons, neural support cells and/or neural support tissues and the administering is prior to the onset of the physical trauma.

2. The method of claim 1, wherein an effective amount of lithium chloride is administered, optionally as a modified release version thereof.

3. The method of claim 1 wherein one or more of (A) and (B) are formulated for administration as a tablet, a capsule, a pill, or an injectable solution.

4. The method of claim 1 wherein one or more of (A) and (B) are formulated for administration via an oral, buccal, mucosal, parenteral, rectal, sub-cutaneous, transdermal, intravenous, intrathecal, intravaginal, nasal, nasal inhalation, pulmonary inhalation, iontophoresis through the skin, iontophoresis through mucosal or buccal membranes, dermal patch, epidural, intracranial, intrapharyngeal, sublingual, intra-articular, intramuscular or a subcutaneous route.

5. The method of claim 1, wherein one or more of (A) and (B) is in the form of one or more of salts, prodrugs, or hydrates, and wherein the compounds are in such a form that they can be safely administered to, given to, or taken by, the subject, and optionally include non-active ingredients selected from excipients, buffers, penetration enhancers, stabilizers, absorption enhancers and carriers.

6. The method of claim 1, wherein the gabapentin is administered in a dosage range of from 5.0 mg to 9,600 mg.

7. The method of claim 1, wherein the progesterone is administered in a dosage range of from 0.05 mg to 1,200 mg.

8. The method of claim 1, wherein the lithium chloride is administered in a dosage range of from 3.0 mg to 3,600 mg.

9. The method of claim 7, wherein the progesterone is administered in a dosage range of 5 mg to 600 mg.

10. The method of claim 1, wherein the gabapentin is administered in a dosage range of 200 mg to 600 mg.

11. The method of claim 1, wherein the trauma is a physical trauma selected from vehicle accidents, workplace accidents, sports accidents, falls, burns, radiation, battlefield injuries, concussive injuries, blast injuries, injuries from landmines, injuries from improvised explosive devices, penetrating injuries, non-penetrating injuries and any traumatic event that can injure, damage, modify, kill or otherwise change the phenotype, gene expression function of a nerve cell, a neural support cell or a neural support tissue.

12. The method of claim 1, wherein the active agents are provided as an initial dose to the subject in accordance with a timing sequence, and wherein the timing sequence begins prior to the onset of the trauma.

13. The method of claim 1, wherein the active agents are provided as a sustaining dose to the subject in accordance with a timing sequence, and wherein the timing sequence begins prior to the onset of trauma.

* * * * *